United States Patent
Odenkirchen

(10) Patent No.: US 7,320,597 B2
(45) Date of Patent: Jan. 22, 2008

(54) VACUUM SEALED SALIVA CONTROL DEVICE

(76) Inventor: Bernard W.S. Odenkirchen, Wassenaarseweg 160, 2223 LD Katwÿk (NL)

( * ) Notice: Subject to any disclaimer, the term of this patent is extended or adjusted under 35 U.S.C. 154(b) by 163 days.

(21) Appl. No.: 11/208,897

(22) Filed: Aug. 22, 2005

(65) Prior Publication Data

US 2007/0042317 A1    Feb. 22, 2007

(51) Int. Cl.
*A61C 17/06*    (2006.01)

(52) U.S. Cl. .................. 433/91; 433/136; 604/316; 248/205.8

(58) Field of Classification Search .................. 433/91, 433/80, 185, 186, 136; 604/314, 315, 316; 248/205.9, 205.8

See application file for complete search history.

(56) References Cited

U.S. PATENT DOCUMENTS

| 765,537 A | | 7/1904 | Abbott | 433/138 |
| 930,236 A | * | 8/1909 | Schacht | 4/255.12 |
| 2,510,184 A | * | 6/1950 | Lynn | 433/186 |
| 2,752,680 A | * | 7/1956 | Winnberg | 433/185 |
| 2,776,489 A | | 1/1957 | McGahee | 433/138 |
| 3,068,868 A | * | 12/1962 | Skopyk | 604/314 |
| 3,460,254 A | * | 8/1969 | Scheuer | 433/8 |
| 4,259,067 A | | 3/1981 | Nelson | 433/93 |
| 4,828,491 A | | 5/1989 | Gray | 433/136 |
| 4,834,110 A | | 5/1989 | Richard | 128/760 |
| 4,998,633 A | | 3/1991 | Schneider | 215/311 |
| 5,865,827 A | | 2/1999 | Bullister | 606/1 |
| 6,213,772 B1 | | 4/2001 | Costello | 433/93 |
| 6,267,591 B1 | | 7/2001 | Barstow | 433/93 |
| 6,752,630 B2 | | 6/2004 | Roetzer | 433/140 |
| 2002/0138109 A1 | | 9/2002 | Keogh et al. | 607/9 |

FOREIGN PATENT DOCUMENTS

| FR | 2844700 | 3/2004 | |
| SU | 1649592 | 5/1991 | |
| WO | 2004/069084 | 8/2004 | 17/6 |

OTHER PUBLICATIONS

Title: Chirurgische behandeling van Aambeien (Hemorrhoiden) Inclusief foto's van behandeling URL: http://www.chirurgenoperatie.nl/pagina/anus/aambeien.php.

* cited by examiner

*Primary Examiner*—Ralph A. Lewis
(74) *Attorney, Agent, or Firm*—Workman Nydegger

(57) ABSTRACT

A saliva control device for controlling or isolating the production of saliva by a salivary gland. The saliva control device includes a body, a cavity formed in the body for forming a seal over the salivary gland, a vacuum chamber in the body that assists the cavity in forming a seal, and an air evacuation passage. The air evacuation passage is used to selectively apply and then maintain a vacuum to the vacuum chamber and cavity.

20 Claims, 7 Drawing Sheets

Fig. 3A                    Fig. 3B

VACUUM SEALED SALIVA CONTROL DEVICE

BACKGROUND OF THE INVENTION

1. The Field of the Invention

The present invention relates to saliva control devices for use in keeping the oral cavity free of saliva so as to facilitate procedures performed by a dental practitioner or oral surgeon.

2. The Relevant Technology

When performing various procedures within the oral cavity, it is often desirable or necessary for the dental practitioner to slow or at least divert the flow of saliva produced by the salivary glands. There are four principle salivary glands within the oral cavity. The two parotid salivary glands are located inside the mouth and near each ear. There are also two sublingual salivary glands located near the base of the tongue. The vast majority of saliva produced enters a patient's mouth through these principle salivary glands. A minor amount also enters through the mucosals. Several devices and techniques have been employed in order to prevent the saliva from interfering with the dental practitioner's work inside the oral cavity.

Rolls of cotton have been used in an attempt to prevent saliva produced by the principle salivary glands from interfering with the work of a dental practitioner within the oral cavity. The cotton roll is placed below the salivary gland. As saliva is produced, it drains downward, and is absorbed by the cotton. One disadvantage of using cotton rolls is that they are rather large and restrict the ability of the dental practitioner to work within the oral cavity because they take up so much space. In addition, they quickly saturate, necessitating removal and replacement of the cotton during the procedure. It is often difficult to maintain the cotton roll in the position placed. Finally, cotton rolls can be uncomfortable for the patient.

Rubber dams have also been used for isolating an area of the mouth from saliva. Rubber dams are difficult to use as they must be assembled, which can take a significant amount of time. In addition, when using a rubber dam, the patient cannot completely close his or her mouth. This makes it difficult for the dental practitioner to check the patient's occlusion, and is generally uncomfortable for the patient.

Dental suction tubes have also been used to remove excess saliva produced by the salivary glands. Generally, the suction tube is inserted periodically to remove excess saliva as it pools in the patient's mouth. This either requires an assistant to periodically insert the suction tube, or it requires interrupting the dental practitioner's work.

Finally, systemic medications (e.g., scapolquinine and atropine) have been used to control the production of saliva. While useful in arresting saliva production, side effects include disorientation, amnesia, and lingering dry mouth.

FIG. 1 illustrates a saliva collection device 10, also called a "Lashley cup," which is used to continuously collect saliva produced by the parotid salivary glands. Lashley cups have not been used to isolate a person's mouth from saliva during dental procedures, perhaps because they require two different vacuum tubes to feed into the patients during use, thereby causing obstruction and discomfort.

In view of the forgoing, it would be an improvement in the art to provide devices for isolating a person's mouth from unwanted saliva produced by the salivary glands while avoiding the discomfort and intrusiveness of conventional devices and methods.

BRIEF SUMMARY OF THE INVENTION

The present invention is directed to a saliva control device for controlling or isolating the production of saliva by a salivary gland. Controlling the production of saliva helps a dental practitioner when working within the oral cavity.

The saliva control device includes a body, a cavity formed in the body for forming a seal over the salivary gland, a vacuum chamber in the body that assists the cavity in forming a seal, and an air evacuation passage. The air evacuation passage is used to selectively apply and then maintain a vacuum to the vacuum chamber and cavity. When under a reduced pressure, the salivary gland is pulled into the cavity. In other words, the vacuum chamber assists the cavity in forming a seal over the salivary gland upon placing the saliva control device over a salivary gland and applying a vacuum to the vacuum chamber and cavity. In this way, the device reduces production of saliva and/or prevents saliva produced from the salivary gland from flowing beyond the confines of the device.

According to one embodiment, the cavity is sufficiently small such that when the salivary gland is pulled up into the cavity the salivary gland is constricted between the walls defining the cavity. This constriction may further control and prevent saliva production.

The saliva control device may be configured to fit over one salivary gland (e.g., a parotid salivary gland) or two salivary glands (e.g., the sublingual salivary glands). Multiple devices may be used simultaneously to cover some or all of a person's salivary glands, as desired. The saliva control device may include a lifeline or leash to prevent the device from inadvertently falling down the patient's throat or otherwise being swallowed. One end of the lifeline is attached to the device (e.g., through an eyelet) and the other end is attached to any suitable anchor so as to prevent the device from being swallowed, choked on, inhaled, or otherwise lost in the event it becomes detached from the inside of the patient's mouth. Examples of suitable lifeline materials include ordinary string, dental floss, and monofilament.

In use, the saliva control device is positioned directly over a person's salivary gland and vacuum adhered such that the salivary gland is pulled into the cavity of the body. A conventional dental suction tube may be used to apply the vacuum, as may any other suction or vacuum device known in the art. One of ordinary skill can select a desired suction device and modify the saliva control device as needed to vacuum seal the device over the salivary gland. With the saliva control device in place, the dental practitioner is able to perform the work needed within the oral cavity without having to worry about the build-up of saliva.

Once the dental practitioner has finished the desired dental procedure, the saliva control device can be removed from the patient's mouth by simply breaking the vacuum (e.g., by prying it off using any suitable flat tool). The saliva control device may remain attached as long as needed, preferably between about 30 minutes and about 3 hours depending upon the procedure performed.

In one embodiment, the suction device is used to position and vacuum adhere the saliva control device over at least one of a person's principle salivary glands. The air evacuation passage of the device is connected to a suitable suction device. The saliva control device may further include a button, a raised rim or a groove near the air evacuation passage for assisting in temporarily connecting the saliva control device to a suction device (e.g., a dental suction tube). If desired, an adhesive may be applied to the bottom of the body of the saliva control device prior to positioning and vacuum-adhering the device over a person's salivary gland. Such an adhesive may aid in adhering the device over the gland and also forming a seal against the oral tissue surface surrounding the gland.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 3A-3C illustrate an alternative embodiment of a saliva control device having two cavities for use over the sublingual salivary glands;

DETAILED DESCRIPTION OF THE PREFERRED EMBODIMENTS

I. Introduction

A detailed description of the invention will now be provided with specific reference to Figures illustrating various exemplary embodiments. It will be appreciated that like structures will be provided with like reference designations.

The present invention is directed to a saliva control device for controlling or isolating the production of saliva by a salivary gland. Controlling or isolating the production of saliva helps a dental practitioner when working within the oral cavity. The saliva control device includes a body, a cavity formed in the body for forming a seal over the salivary gland, a vacuum chamber in the body that assists the cavity in forming a seal, and an air evacuation passage. The air evacuation passage is in fluid communication with the vacuum chamber, which is in communication with the cavity. The air evacuation passage is used to selectively apply and then maintain a vacuum to the vacuum chamber and cavity. When under a reduced pressure the salivary gland is pulled into the cavity. In this way the device reduces production of saliva and/or prevents saliva produced from the salivary gland from flowing beyond the confines of the device. Alternative saliva control devices are disclosed in PCT Patent Application Publication No. WO2004069084 titled "VACUUM SEALED SALIVA CONTROL DEVICE", hereby incorporated by reference.

II. Exemplary Vacuum Sealed Saliva Control Devices

Figure 1:
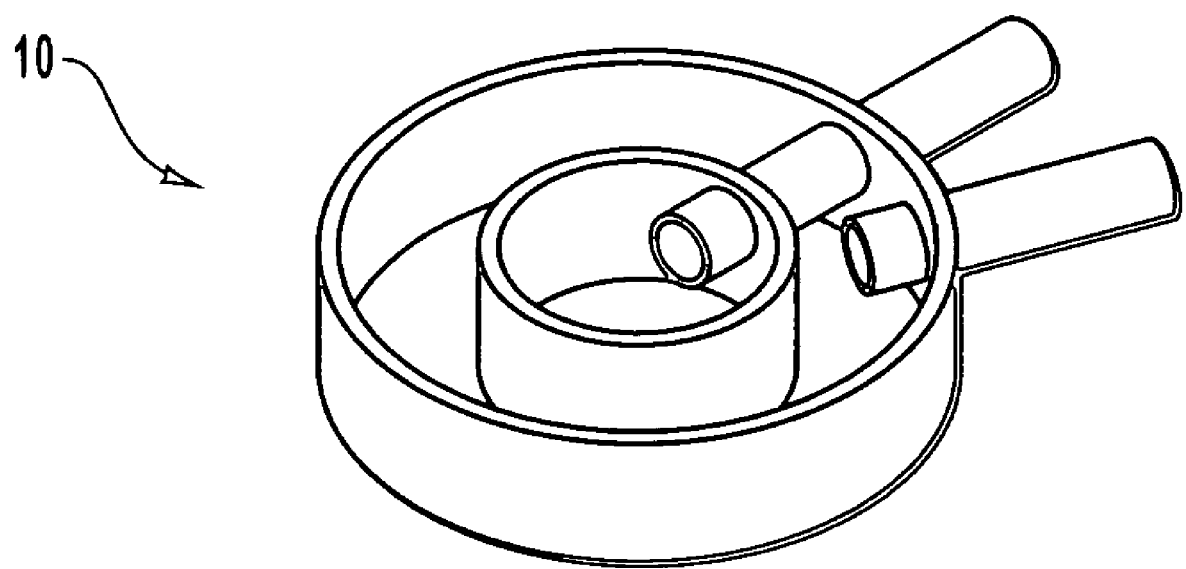
FIG. 1 illustrates a perspective view of an existing saliva collector device.
Figure 2A:
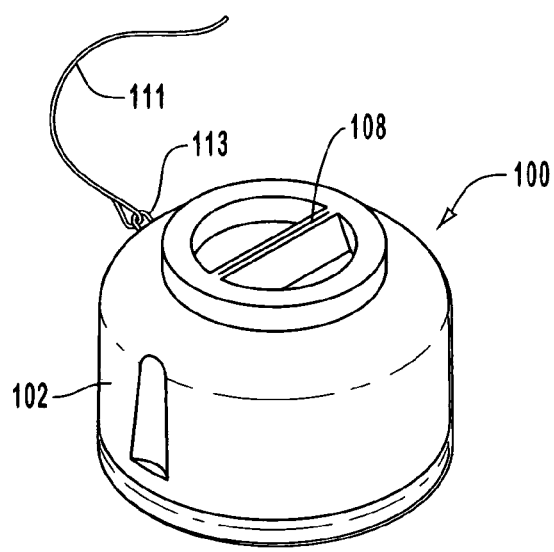
FIGS. 2A and 2B illustrate top and bottom views of an exemplary embodiment of a vacuum sealed saliva control device.
Figure 2B:
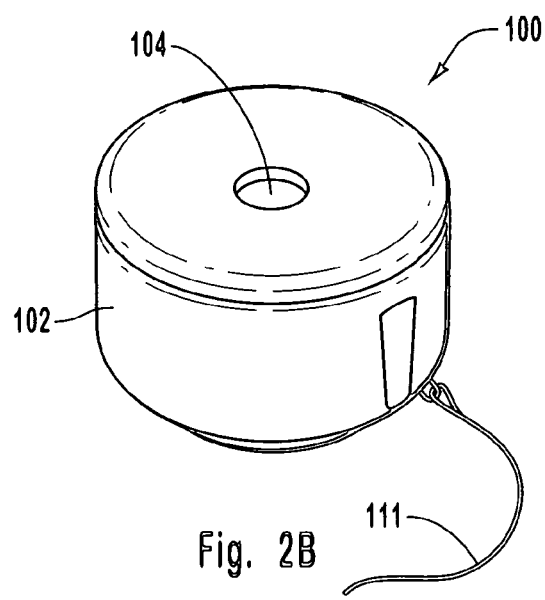
Figure 2C:
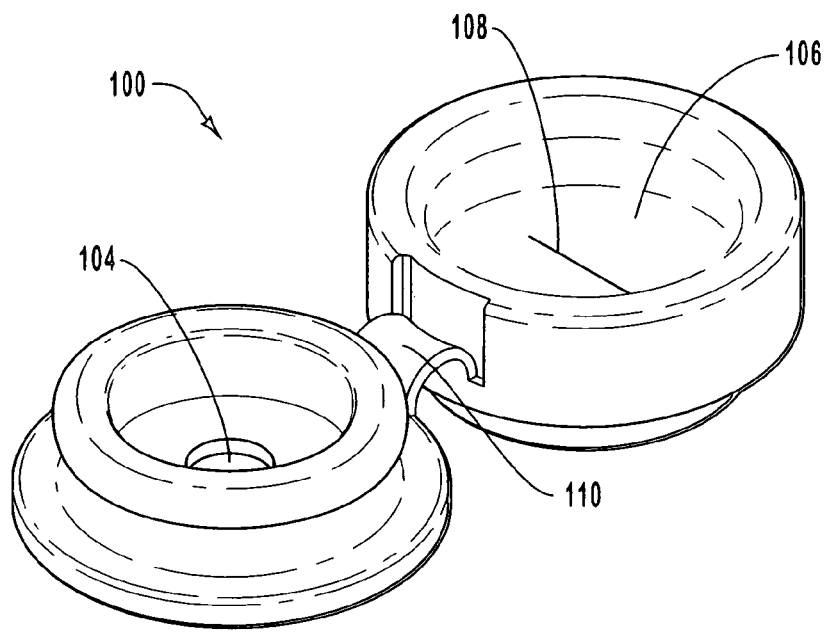
FIG. 2C illustrates an embodiment of the saliva control device of FIGS. 2A and 2B that can be formed as a single integral piece.
Figure 4A:
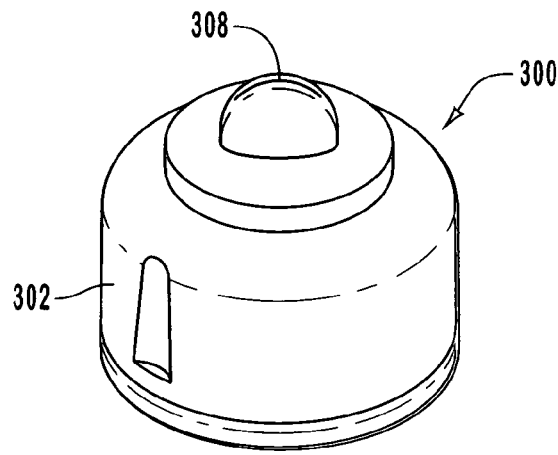
FIGS. 4A-4C illustrate an alternative embodiment of a saliva control device having a single large cavity for use over the sublingual salivary glands.
Figure 4B:
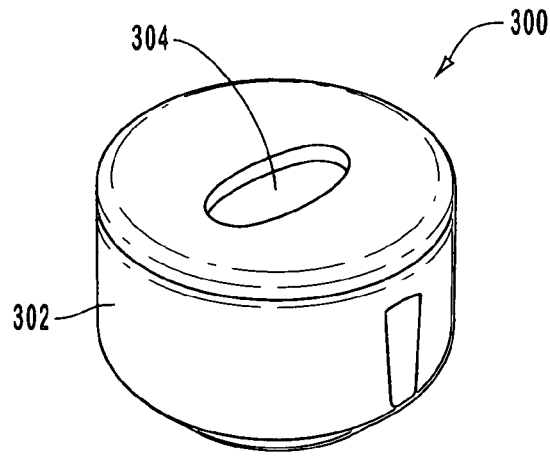
Figure 4C:
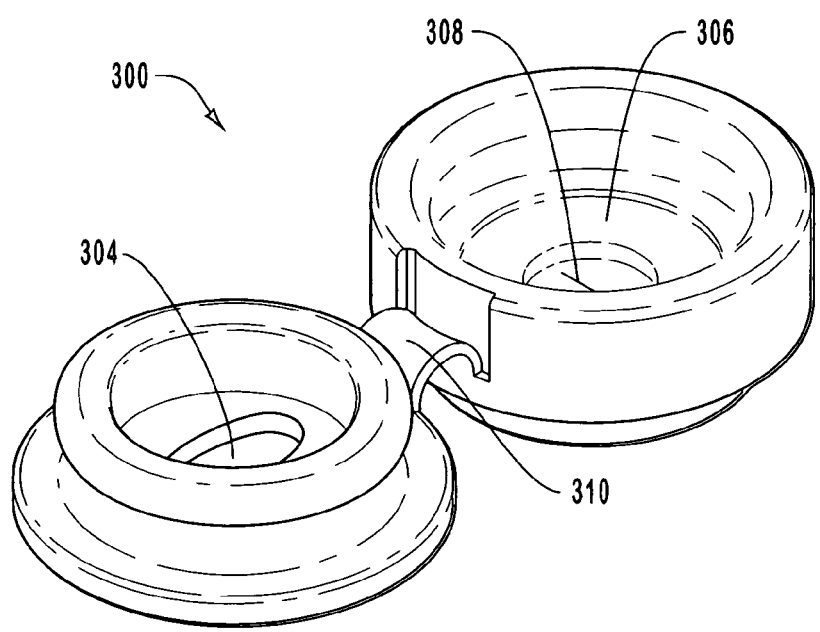

FIGS. 2A-2C illustrate an exemplary saliva control device 100. FIGS. 2A and 2B are top and bottom perspective views, while FIG. 2C is a side perspective view. Device 100 includes a body 102, a cavity 104 (FIG. 2B), a vacuum chamber 106, and an air evacuation passage 108 (FIG. 2A). Although illustrated as being substantially circular in FIGS. 2A-2C, the body 102 and cavity 104 may be of any desired shape. An embodiment that includes a cavity of a different shape is illustrated in FIGS. 4A-4C. Returning to FIGS. 2A-2C, body 102 includes a substantially flat, planar bottom surface for placement against oral tissue surrounding a salivary gland. An opening in the form of cavity 104 is formed through the bottom surface of body 102 so that cavity 104 is configured for forming a seal over a salivary gland. According to one embodiment, the body 102 surrounding cavity 104 may be formed of a soft, adaptable material. In addition to forming a tight seal, a soft flexible material may provide a higher degree of comfort for the patient.

As best seen in FIG. 2B, the air evacuation passage 108 is located near the center of the top of body 102 so as to be easily accessible to the dental practitioner during placement of the device. It is preferable for the air evacuation passage 108 to be located near the center of the top of body 102, although it may alternatively be located elsewhere on the device.

Air evacuation passage 108 (FIG. 2A) is configured so as to selectively evacuate air from vacuum chamber 106 and cavity 104, allowing the dental practitioner to vacuum adhere device 100 over a person's salivary gland. The saliva control device may be formed as a single integral piece. One such embodiment is illustrated in FIG. 2C where the body comprises two integral portions connected by a flexible hinge 110.

The saliva control device 100 may include a lifeline (or leash) 111 to prevent the device 100 from inadvertently falling down the patient's throat or being inhaled. One end of the lifeline 111 is attached to device 100, such as through a depression or protrusion (e.g., through eyelet 113), and the other end is attached to any suitable anchor (e.g., a dental device external to the patient's mouth) so as to prevent device 100 from being swallowed, choked on, inhaled, or otherwise lost in the event it becomes detached from the inside of the patient's mouth. Examples of suitable lifeline materials include ordinary string, dental floss, and monofilament.

Figure 3C:
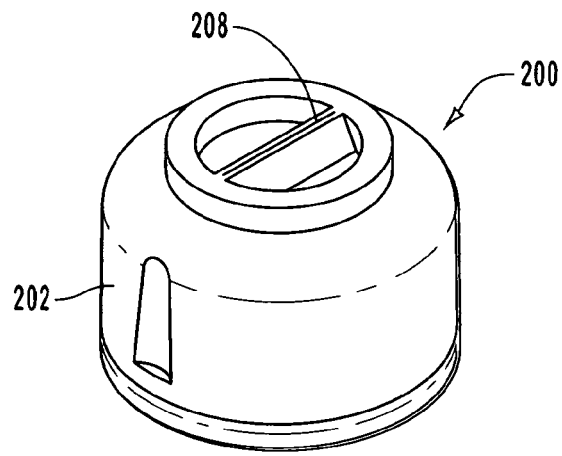
Figure 3C:
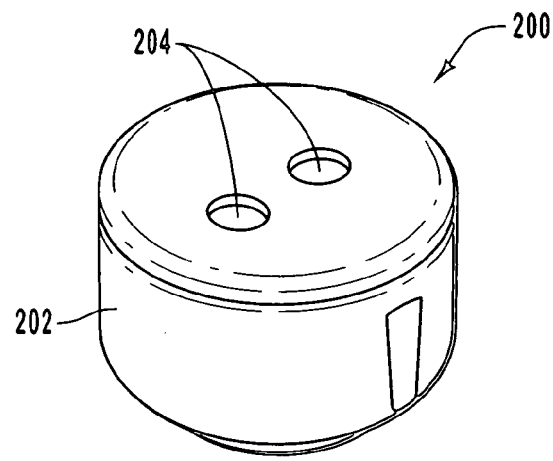
Figure 3C:
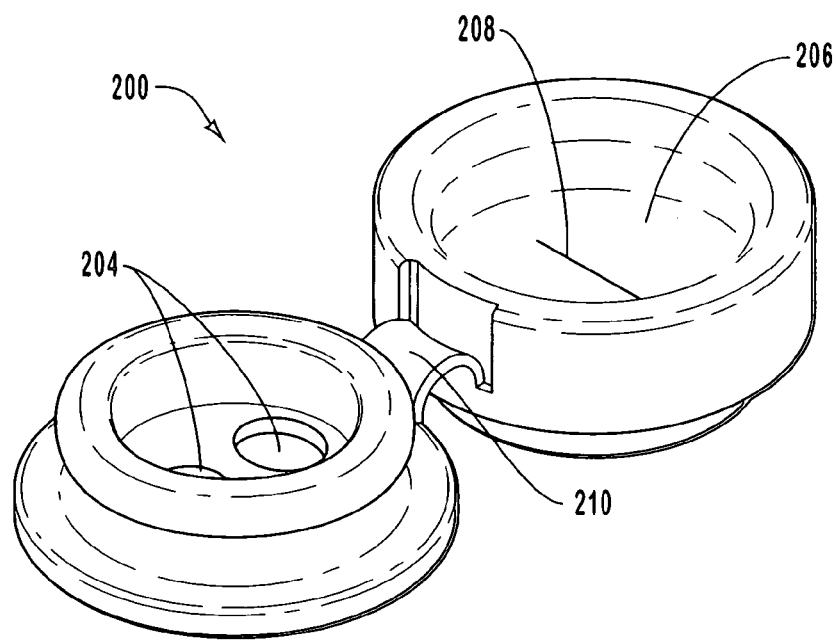

FIGS. 3A-3C illustrate an alternative saliva control device 200. FIGS. 3A and 3B are top and bottom perspective views, while FIG. 3C illustrates a view of device 200 formed as a single integral piece where the device is in an "open" position. The "open" position is shown in order to better illustrate how the device 200 may be formed as a single integral piece. The device 200 includes a body 202, a pair of cavities 204 (FIG. 3B), a vacuum chamber 206, an air evacuation passage comprising a one-way slit valve 208 (FIG. 3A), and a flexible hinge 210. The inclusion of two cavities 204 within device 200 may be particularly useful for use over the sublingual salivary glands, allowing one device to be used to control saliva production from both glands.

FIGS. 4A-4C illustrate another alternative saliva control device 300 which includes a body 302, a large oval cavity 304 (FIG. 4B), a vacuum chamber 306, an air evacuation passage 308 (FIG. 4A), and a flexible hinge 310. Cavity 304 is configured to receive two salivary glands (e.g., both sublingual glands). Although illustrated as being substantially oval, cavity 304 could be of any appropriate shape (e.g., large round or other). Cavity 304 is in fluid communication with vacuum chamber 306, which is in communication with air evacuation passage 308 such that vacuum chamber 306 assists cavity 304 in forming a seal over one or more salivary glands.

Figures 5A, 5B:
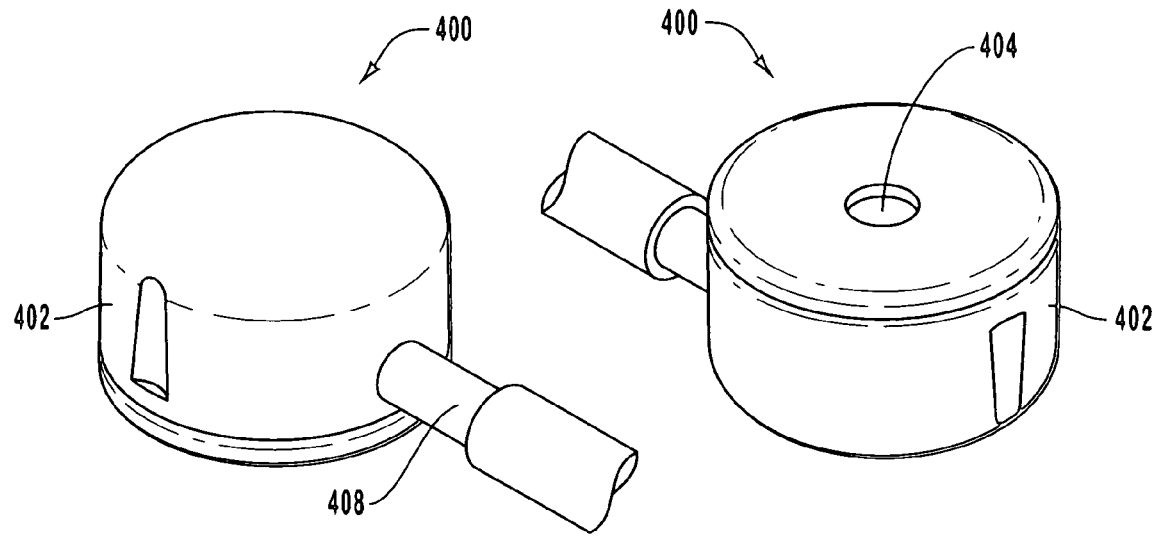
FIGS. 5A-5C illustrate another alternative embodiment of a saliva control device having an air evacuation passage comprising a tube.
Figure 5C:
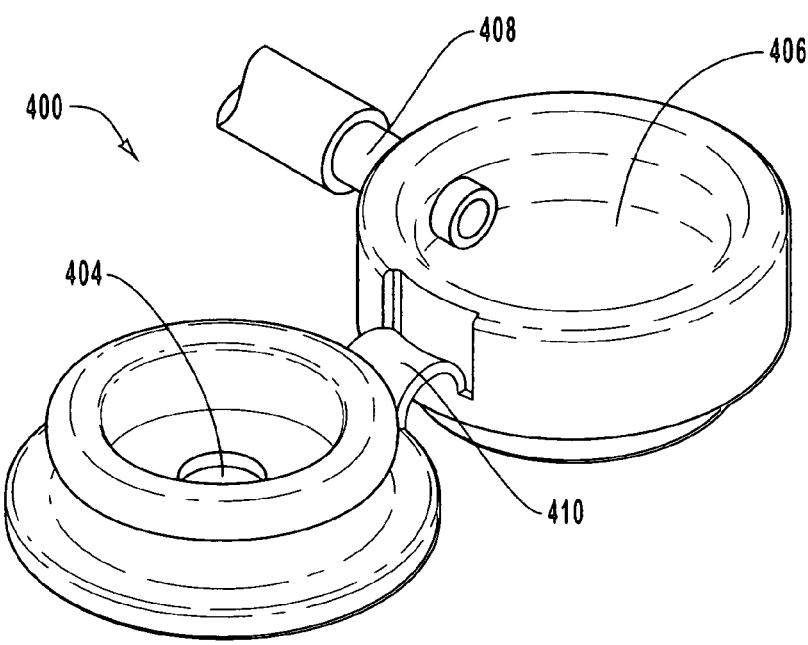

FIGS. 5A-5C illustrate another saliva control device 400, including a body 402, a cavity 404 (FIG. 5B), a vacuum chamber 406 in the body 402, and an air evacuation passage 408 (FIG. 5A). Cavity 404 is in fluid communication with vacuum chamber 406 such that vacuum chamber 406 assists cavity 404 in forming a seal over a salivary gland. The illustrated embodiment of air evacuation passage 408 comprises a side port located on a side of the device, although various other structures of air evacuation passages could alternatively be used. FIG. 5C illustrates an embodiment of device 400 formed as a single integral piece having two portions connected by a flexible hinge 410.

Figure 6A:
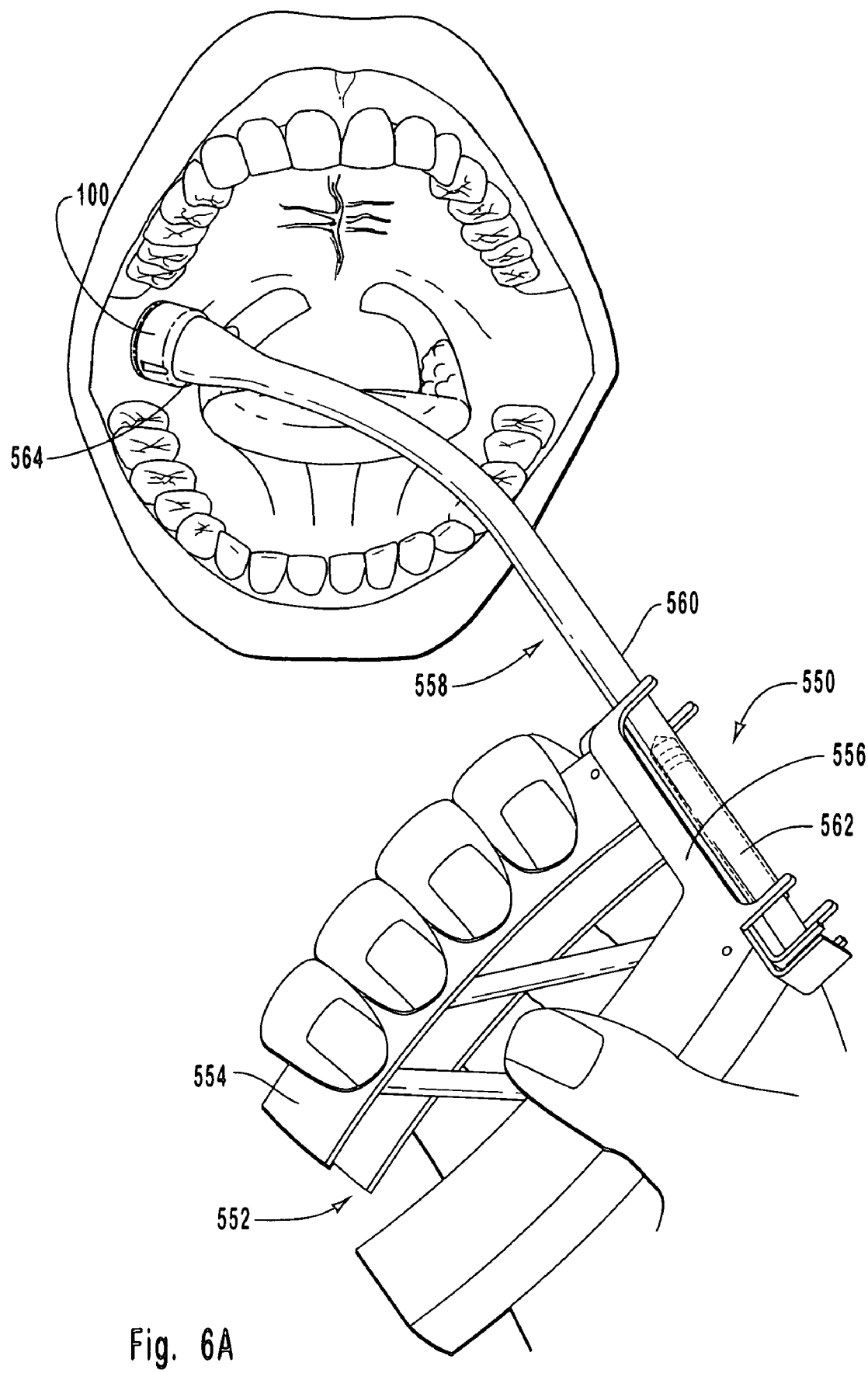
FIGS. 6A and 6B illustrate placement of exemplary vacuum sealed saliva control devices within a person's mouth.

FIG. 6A illustrates an exemplary use of a hand-held suction tool 550 being used to position and vacuum-adhere saliva control device 100 over one of a patient's parotid salivary glands. Suction tool 550 includes a body 552 having a handle 554, with an upper portion 556 of the body 552 being configured to cradle an application syringe 558. Application syringe 558 includes a barrel 560, a plunger 562, and a tip 564. Tip 564 is configured to couple to air evacuation passage 108 and optional surrounding structure (e.g., a button, a raised rim or a groove) of device 100 (see FIG. 2A). Upon manipulation of handle 554, a vacuum of sufficient strength is applied so as to cause device 100 to vacuum-adhere over the salivary gland. Application syringe 558 may be disposable or autoclavable so as to prevent cross contamination between patients.

Figure 6B:
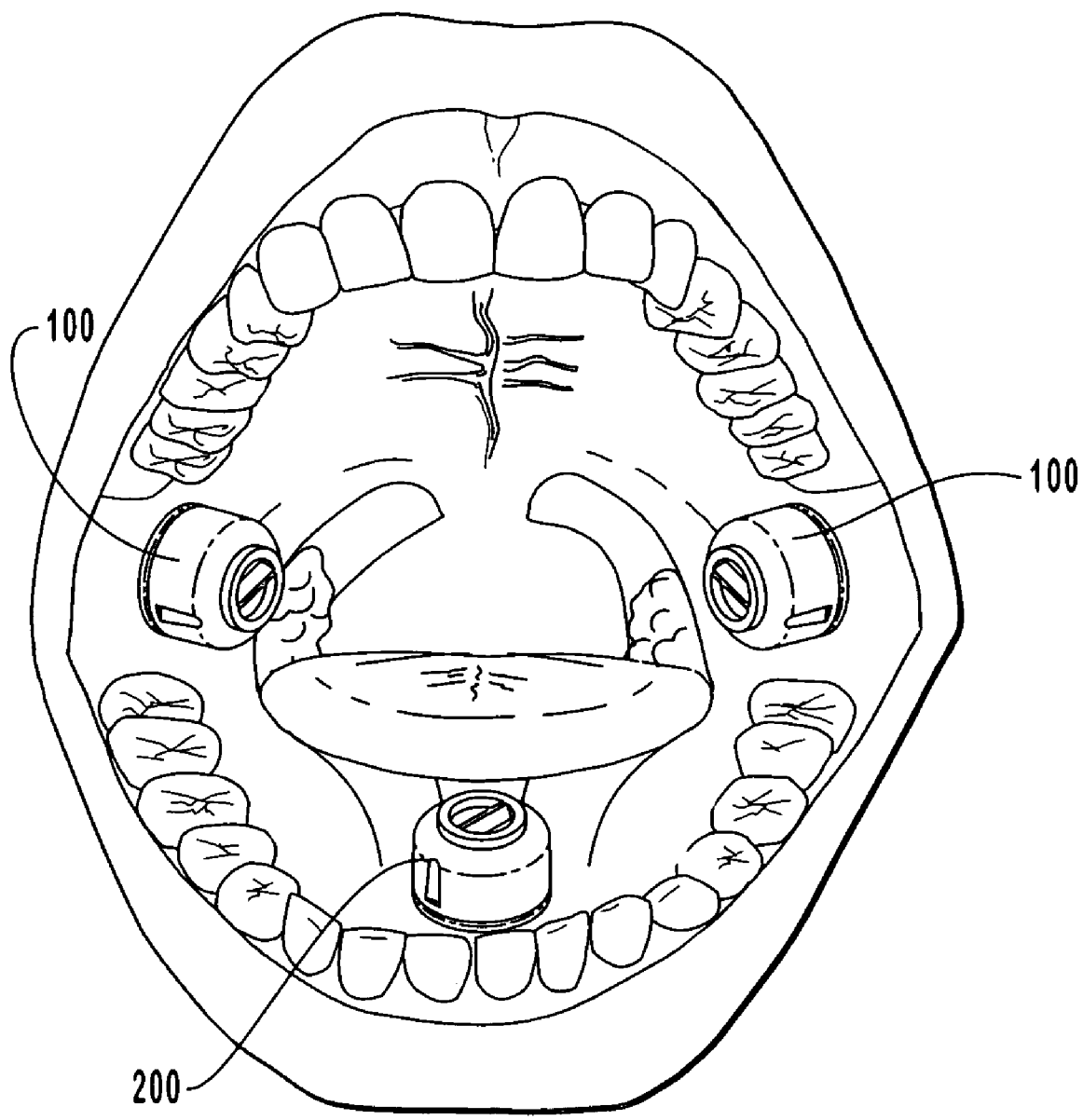

FIG. 6B illustrates a plurality of saliva control devices 100, 100, and 200 positioned and vacuum-adhered over the patient's salivary glands. Two identical devices 100 have been positioned over the patient's parotid salivary glands, while device 200 has been placed and vacuum adhered over the patient's sublingual salivary glands. Although illustrated in a configuration where all of the principle salivary glands are covered, any number of devices may be used (e.g., as little as one or as many as three). Once the dental practitioner has finished working within the oral cavity, the devices may be removed from the inside of the patient's mouth by simply breaking the vacuum (e.g., by prying the device off using a flat tool).

If desired, an adhesive may be applied to the bottom of the body of the saliva control device prior to positioning and vacuum adhering the device over a person's salivary gland. Examples of suitable adhesives include, but are not limited to polyvinylpyrrolidone, carboxymethylcellulose, carbopol, or a light curable adhesive (e.g., one or more of a hydrophilic polyurethane, a hydrophilic acrylic, or a hydrophilic polyurethane-acrylic).

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A saliva control device for placement over a salivary gland and surrounding oral tissue for controlling production of saliva by the salivary gland comprising:
    a body having a substantially flat, planar bottom surface for placement against oral tissue surrounding a salivary gland, said flat, planar bottom surface having an opening formed therethrough in the form of a cavity that is sufficiently small so that when the salivary gland is pulled into the cavity the salivary gland is constricted to help control and prevent saliva production;
    said body also defining a vacuum chamber within the body that is in fluid communication with the cavity so that upon applying a vacuum to the vacuum chamber, the applied vacuum will assist in pulling the salivary gland through the opening that defines the cavity in order to constrict and seal the salivary gland within the cavity; and
    an air evacuation passage in fluid communication with the vacuum chamber through which the vacuum is applied to the vacuum chamber, the air evacuation passage comprising a one-way valve for sealing the evacuation passage after the vacuum has been applied.

2. A saliva control device as recited in claim 1, wherein the air evacuation passage is located on the top of the body.

3. A saliva control device as recited in claim 2, wherein the air evacuation passage is located near the center of the top of the body.

4. A saliva control device as recited in claim 1, further comprising at least one of a button, a raised rim, or a groove formed near the air evacuation passage for assisting in releasable connecting the saliva control device to a sectioning device for applying a vacuum to the air evacuation passage and vacuum chamber.

5. A saliva control device as recited in claim 4, wherein the one-way valve comprises a slit formed in a button.

6. A saliva control device as recited in claim 1, further comprising at least one of a depression or protrusion formed on the body for attaching a lifeline to the body.

7. A saliva control device as recited in claim 6, further comprising a lifeline attached to the body.

8. A saliva control device as recited in claim 1, wherein the body surrounding the opening is formed of a soft, adaptable material.

9. A saliva control device as recited in claim 1, wherein the opening is substantially circular.

10. A saliva control device as recited in claim 1, wherein the opening is sized and configured so as to receive and constrict around one salivary gland.

11. A saliva control device as recited in claim 1, wherein the opening is sized and configured so as to receive and constrict around two salivary glands.

12. A saliva control device as recited in claim 1, further comprising a second opening, and wherein each opening is configured to receive and constrict around a respective salivary gland.

13. A saliva control device as recited in claim 1, wherein the body comprises two integral portions connected by a flexible hinge such that the device is formed as a single integral piece.

14. A method of using a saliva control device comprising:
    providing a saliva control device as recited in claim 1;

positioning the saliva control device such that the opening formed through the bottom surface of the body is positioned directly over a person's salivary gland;

applying a vacuum to the one-way valve and vacuum chamber so that the applied vacuum assists in pulling the salivary gland through the opening, the body surrounding the opening constricting around the salivary gland so as to vacuum adhere the saliva control device over the salivary gland so as to help control and prevent saliva production and to block saliva flow from the salivary gland into the intra-oral cavity; and removing the saliva control device.

15. A method as recited in claim 14, wherein the saliva control device is vacuum adhered over a parotid salivary gland.

16. A method as recited in claim 14, wherein the saliva control device is vacuum adhered over the sublingual salivary glands.

17. A method as recited in claim 14, further comprising applying an adhesive to the bottom surface of the body of the saliva control device prior to positioning and vacuum adhering the device over a person's salivary gland.

18. A method as recited in claim 17, wherein the adhesive comprises at least one of polyvinylpyrrolidone, carboxymethylcellulose, or carbopol.

19. A method as recited in claim 17, wherein the adhesive is a light curable adhesive comprising at least one of a hydrophilic polyurethane, a hydrophilic acrylic, or a hydrophilic polyurethane-acrylic.

20. A method as recited in claim 14, wherein the saliva control device is removed after a time period of about 30 minutes to about 3 hours.

* * * * *

UNITED STATES PATENT AND TRADEMARK OFFICE
CERTIFICATE OF CORRECTION

PATENT NO. : 7,320,597 B2  
APPLICATION NO. : 11/208897  
DATED : January 22, 2008  
INVENTOR(S) : Odenkirchen Page 1 of 1

It is certified that error appears in the above-identified patent and that said Letters Patent is hereby corrected as shown below:

Column 1
Line 63, change "forgoing" to --foregoing--

Column 3
Line 6, change "full" to --fully--

Column 4
Line 11, after "view" insert --of device 100 formed as a single integral piece where the device is in an "open" position--
Line 28, change "2B" to --2A--

Column 6
Line 36, change "releasable" to --releasably--
Line 36, change "sectioning" to --suctioning--

Signed and Sealed this

Ninth Day of September, 2008

JON W. DUDAS  
*Director of the United States Patent and Trademark Office*